(12) United States Patent
Eipel

(10) Patent No.: US 6,234,033 B1
(45) Date of Patent: May 22, 2001

(54) AUTOMATIC PIPETTING APPARATUS

(75) Inventor: Heinz Eipel, Bensheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/301,578

(22) Filed: Apr. 29, 1999

(30) Foreign Application Priority Data

May 25, 1998 (DE) .............................. 198 23 283

(51) Int. Cl.[7] .................................................. G01N 35/10
(52) U.S. Cl. .................... 73/864.25; 422/65; 422/100
(58) Field of Search .......................... 73/864.17, 864.18, 73/864.24, 864.25; 422/65, 100

(56) References Cited

U.S. PATENT DOCUMENTS 3,853,008 * 12/1974 Hoffa et al. ..................... 73/423 R
4,812,392 * 3/1989 Miyake et al. ........................ 435/3
5,306,510 * 4/1994 Meltzer ................................ 422/65
5,443,791 * 8/1995 Cathcart et al. .................... 422/65
5,897,837 * 4/1999 Mizuno ............................. 422/100
5,906,795 * 5/1999 Nakashima et al. .............. 422/100
5,985,214 * 11/1999 Stylli et al. ......................... 422/65
6,132,582 * 10/2000 King et al. ....................... 422/100

* cited by examiner

Primary Examiner—Hezron Williams
Assistant Examiner—C. D. Garber
(74) Attorney, Agent, or Firm—Keil & Weinakuf

(57) ABSTRACT

The invention relates to an automatic pipetting apparatus, having a drive for moving a pipetting instrument from a source site to a target site, in which apparatus end stops (8–10, 14, 15), which can be finely adjusted automatically, for the movements of the pipetting instrument (1) generated by the drive are provided at the source site and/or the target site.

9 Claims, 1 Drawing Sheet

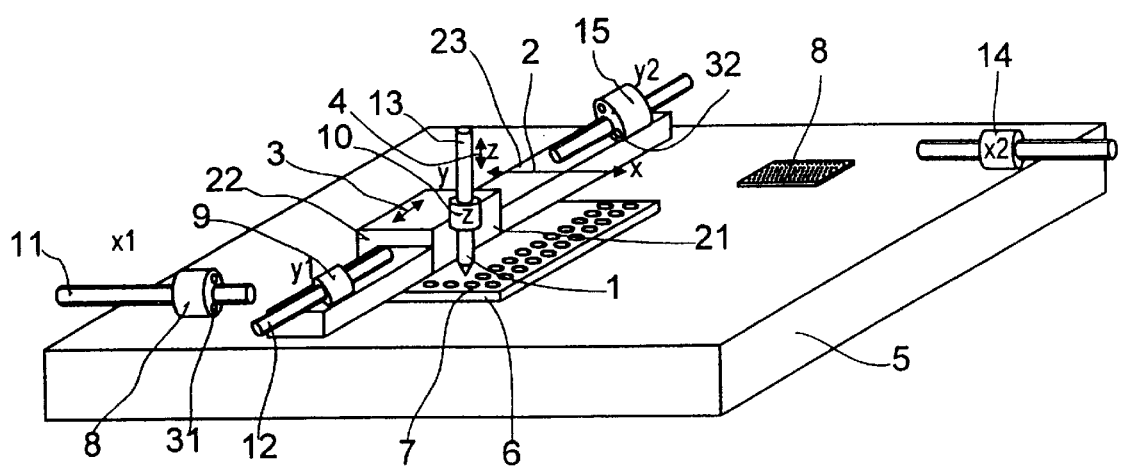

AUTOMATIC PIPETTING APPARATUS

The invention relates to an automatic pipetting apparatus, having a drive for moving a pipetting instrument from a source site to a target site, which apparatus is used, for example, for mass screening in order to discover new lead structures in particular for pharmacology and crop protection.

At the moment, it is generally customary for the substances to be tested to be presented to an automatic testing apparatus in the Mikrotiter Format (with 96 to 1536 wells per plate). From this presentation arrangement, the substances have to be transferred separately to the individual analysis sites using an automatic pipetting apparatus. Also, as the tests progress, further pipetting steps are required although in general these may be carried out together rather than separately for each analysis site. The pipetting of individual substances when carrying out mass screening tests is particularly time-consuming. Screening with so-called spot arrays also requires an enormous number of individual pipetting steps.

The automatic pipetting apparatus which are currently customary guide the pipetting instrument over a work surface with one drive each for the x-, y- and generally also the z-axes. According to the prior art, it is possible, in principle, to establish various types of drive. For example, one drive used is a stepper motor which transmits a linear movement via a recirculating ball screw. The advantage of this type of drive is the very high level of accuracy combined with relatively low costs. The main drawback is the fact that the linear movement is extremely slow, even if a speed ramp with different speeds is passed through during the actual adjustment operation.

In addition, DC motor drives with a resistive, inductive or capacitive sensor or with an optical linear guide are used for position feedback. These drives are significantly quicker than stepper motors, but are complex and therefore expensive.

In principle, the same advantages and disadvantages also apply to linear motors used as an alternative to rotating motors.

The invention relates to an automatic pipetting apparatus which avoids the drawbacks of previous arrangements while achieving high pipetting speeds.

According to the invention, it is possible to divide the linear movement into a rapid movement over a relatively long distance between source site and target site, end stops, which can be finely adjusted automatically, being arranged with a high level of accuracy at both the source site and the target site. The adjustable end stops, which normally only have to be adjusted by a few millimeters or a few hundred micrometers, combined with the rapid movement result in an enormous increase in the transfer rate.

Arranging shock-absorbing means on the end stops decelerates the rapid movement before the stop is reached. It is thus possible to avoid impacts.

Preferably, the drive is designed as a hydraulic or pneumatic linear drive and is therefore inexpensive when moving rapidly.

In order to feed back information concerning arrival at the end stops, sensors for position detection may be arranged in the area of the end stops, which sensors register the arrival of the pipetting instrument at the end stops and, if appropriate, feed this information to a control unit or memory unit. To counteract having to wait for the end of the transient mechanical effect caused by the stop, the speed is increased again.

Finally, it is possible to use end stops with different adjustment accuracies, allowing the costs to be reduced further, since hitherto the highest adjustment accuracy of one individual direction of movement was decisive for the entire system.

The invention also relates to a method with which the pipetting speeds are increased significantly, which is achieved by means of the mutually independent adjustment within short distances of the end stop and the relatively long distances.

In a refinement of the method, the rapid movement is decelerated before the end stop is reached, it being possible, furthermore, to measure the position of the pipetting instrument after the end stop has been reached and, if appropriate, to carry out a correction in the event of positional inaccuracies.

The drawing shows a diagrammatic sketch of an automatic pipetting apparatus according to the invention.

The automatic pipetting apparatus has a pipetting instrument 1 which can be moved over a work surface 5 in three axes 2, 3, 4 in the x-, y- and z-directions.

A substance bank plate 6, which has a plurality of wells 7 for substances, is arranged on the work surface 5. Furthermore, a specimen slide 8, to which the substances contained in the plate 6 are to be applied, is arranged on the work surface 5.

At the source site, a well 7 in the plate 6, the pipetting instrument 1 is brought to bear against stops 8, 9, 10, it being possible to adjust the end stops 8, 9, 10 via a spindle drive 11, 12, 13.

At the target site, a point on the specimen slide 8, the pipetting instrument 1 is again brought to bear against adjustable end stops 14, 15 (x2, y2), the drive for actually moving the pipetting instrument not being shown.

The pipetting instrument 1 is attached to a holder 21 which can be displaced in the direction of the z-axis, For its part, this holder 21 is arranged on a carriage 22 which is mounted so that it can be displaced on a bar 23 in the direction of the yaxis 3. For its part, the bar 23 is mounted and driven so that it can be moved in the direction of the x-axis 2, in a manner which is not shown.

In order to overcome the problems presented by the long distances, the drive (not shown) used is a hydraulic or pneumatic drive, in which case the drive elements may be simple cylinders with pistons. An advantage of this solution is the low mass and robustness of the drive element, with the result that the movements can be carried out particularly quickly. Although in principle the adjustable end stops allow position feedback to be dispensed with, sensors 31, 32 for confirming that the carriage 22 or the bar 23 is bearing against the end stops are provided in the end stops 8, 15, in order to avoid a pipetting instrument which is not yet in the final position from delivering or collecting substances incorrectly.

The arrangement of accurate end stops 8 to 10, 14, 15, which can be moved by stepper motors, both at the source site and at the target site, and for each of the individual axes 2, 3, 4, results in a substantial increase in the pipetting rates, since the end stops only have to undergo minimal adjustment between the individual pipetting operations. The relatively long distances between source site and target site can be covered by means of an electric, hydraulic or preferably pneumatic drive.

Furthermore, a hydraulic or pneumatic damping cylinder, which decelerates the rapid movement just as the respective preset stop is reached and prevents impacts, may be arranged on the end stops. This is not shown in the drawing.

The principal application is a "reformatting" of analyses which are to be carried out in parallel from microtiter plate format to a nano-format with a few thousand analysis points, e.g. on a specimen slide which is customarily used in microscopy.

The end stops x1 and y1, which are, for example, driven by stepper motors, fix the sites of the wells 7 of the microtiter plate 6, which is regarded as the source for the substances which are to be pipetted. The fine-resolution end stops x2 and y2 determine the target sites on the specimen slide. In this case, the resolution accuracy of the end stops in question may be a function of the positional accuracy required. For example, a lower level of accuracy can be set for the approach to the relatively low (grid) resolution wells at the source site than at the high-resolution analysis points on the specimen slide at the target site. This feature is particularly advantageous compared to systems known hitherto.

I claim:

1. An automatic pipetting apparatus, having a drive for moving a pipetting instrument (1) from a source site to a target site, wherein end stops (8–10, 14, 15), which can be finely adjusted automatically, for the movements of the pipetting instrument (1) generated by the drive are provided at the source site and/or the target site.

2. An automatic pipetting apparatus as claimed in claim 1, wherein shock-absorbing means are arranged on the end stops (8–10, 14, 15).

3. An automatic pipetting apparatus as claimed in claim 1 wherein the drive is designed as a hydraulic or pneumatic linear drive.

4. An automatic pipetting apparatus as claimed in claim 1 wherein the end stops (8–10, 14, 15) have stop faces which are controlled by stepper motors.

5. An automatic pipetting apparatus as claimed in claim 1, wherein sensors (31, 32) for position detection are arranged on the end stops (8–10, 14, 15).

6. An automatic pipetting apparatus as claimed in claim 1, wherein the end stops (8, 9) of the source site have a different adjustment accuracy from the end stops (14, 15) of the target site.

7. A method for automatic pipetting, comprising collection of a substance at a source site and delivery of the substance at a target site, and the movement of the pipetting instrument from the source site to the target site, wherein the pipetting instrument is moved rapidly from the source site, and wherein end stops, the position of which can be varied, are in the mean time moved into an accurate position at the target site, the movements being locally independent of one another.

8. A method as claimed in claim 7, wherein the rapid movement is decelerated before the end stop is reached.

9. A method as claimed in claim 7 wherein the position of the pipetting instrument is measured after the end stop has been reached.

* * * * *